United States Patent [19]
de la Chapelle et al.

[11] Patent Number: 5,851,768
[45] Date of Patent: Dec. 22, 1998

[54] METHOD FOR DIAGNOSIS OF OVARIAN DYSGENESIS

[75] Inventors: Albert de la Chapelle, Helsinki; Ilpo Huhtaniemi, Turku; Kristiina Aittomäki, Helsinki, all of Finland

[73] Assignee: Helsinki University Licensing, Ltd., Helsinki, Finland

[21] Appl. No.: 531,070

[22] Filed: Sep. 20, 1995

[51] Int. Cl.[6] .............................. C12Q 1/68; C12P 19/34; C07H 21/02; C07H 21/04

[52] U.S. Cl. ......................... 435/6; 435/91.2; 536/23.1; 536/24.3; 536/24.33

[58] Field of Search .................... 435/6, 91.2; 536/23.1, 536/24.3, 24.33

[56] References Cited

PUBLICATIONS

Aiman et al., "Premature Ovarian Failure," *Obstet. Gynecol.*, 66(1):9–14 (Jul. 1985).
Aittomäki, K., "The Genetics XX Gonadal Dysgenesis," *Am. J. Hum Genet.*, 54:844–851 (1994).
Catt et al., "Receptors for Gonadotropic Hormones," in *Methods in Receptor Research*, Chapter 9, (Belcher, Ed.), pp. 175–250 (1976).
Chelly et al., "Illegitimate Transcription: Transcription of Any Gene in Any Cell Type," *Proc. Nat'l. Acad. Sci.* (USA), 86:2617–2621 (Apr. 1989).
Chomczynski et al., "Single–Step Method of RNA Isolation by Acid Guanidinium Thiocyanate–Phenol–Choloroform Extraction," *Anal. Biochem.*, 162:156–159 (1987).
Davis et al., "Identification of the Sites of N–Linked Glycosylation on the Follicle–Stimullating Hormone (FSH) Receptor and Assessment of their Role in FSH Receptor Function," *Molecular Endocrinology*, 9(2):159–170 (1995).
de la Chapelle, A., "Disease gene mapping in isolated human populations: the example of Finland," *J. Med. Genet.*, 30:857–865 (1993).
Ellington, "Purification of Oligonucleotides Using Denaturing Polyacrylamide Gel Electrophoresis," in *Current Protocols in Molecular Biology*, (Ausubel et al., Eds), John Wiley & Sons, Inc., pp. 2.12.1–2.12.5 (1993).
Granat et al., "Familial gonadal germinative failure: endocrine and human leukocyte antigen studies," *Fertility and Sterility*, 40(2):215–219 (Aug. 1983).
Gromoll et al. "Localization of the human FSH receptor to chromosome 2 p21 using a genomic probe compromising exon 10," *J. Mol. Endocrinology*, 12:265–271 (1994).
Gromoll et al., "Molecular Cloning of the Testicular Follicle Stimulating Hormone Receptor of the Non Human Primate Macaca Fascicularis and Identification of Multiple Transcripts in the Testis," *Biochem. Biophys. Res. Comm.*, 196(3):1066–1072 (Nov. 15, 1993).
Gudermann et al., "In Vitro Bioassay for Human Serum Follicle–Stimulating Hormone (FSH) Based on L Cells Transfected with Recombinant Rat FSH Receptor: Validation of a Model System," *Endocrinology*, 135(5):2204–2213 (1994).
Gyapay et al., "The 1993–94 Généthon human genetic linkage map," *Nature Genetics*, 7:246–339 (Jun. 1994).
Halpin et al., "Effects of gonadotropin deficiency on follicular development in hypogonadal (hpg) mice," *J. Reprod. Fert.*, 78:119–125 (1986).
Harper et al., "Femtomole Sensitive Radioimmunoassay for Cyclic AMP and Cyclic GMP After 2'0 Acetylation by Acetic Anhydride in Aqueous Solution," *J. Cycl. Nucleotide Res.*, 1:207–218 (1975).

(List continued on next page.)

*Primary Examiner*—W. Gary Jones
*Assistant Examiner*—Dianne Rees
*Attorney, Agent, or Firm*—Marshall, O'Toole, Gerstein, Murray & Borun

[57] ABSTRACT

Methods are provided for diagnosing ovarian dysgenesis, comprising analysis of DNA from a patient which encodes a portion of the receptor for follicle-stimulating hormone.

19 Claims, 14 Drawing Sheets

OTHER PUBLICATIONS

Heckert et al., "Structural Organization of the Follicle–Stimulating Hormone Receptor Gene," *Molecular endocrinology*, 6(1):70–80 (1992).

Kozak, M. "The Scanning Model for Translation: An Update," *J. Cell Biol.*, 108:229–241 (Feb. 1989).

LaPolt et al., "Gonadotropin–Induced Up–and Down–Regulation of Ovarian Follicle–Stimulating Hormone (FSH) Receptor Gene Expression in Immature Rats: Effects of Pregnant Mare's Serum Gonadotropin, Human Chorionic Gonadotropin, and Recombinant FSH," *Endocrinology*, 130(3):1289–1295 (1992).

Lathrop et al., "Strategies for multilocus linkage analysis in humans," *Proc. Nat'l. Acad. Sci. (USA)*, 81:3443–3446 (Jun. 1984).

Leach et al., "Three dinucleotide repeat polymorphisms proximal to the D2S123 locus," *Hum. Mol. Genet.*, 3(11):2082 (1994).

Lerman et al., "Computational Simulation of DNA Melting and Its Application to Denaturing Gradient Gel Electrophoresis," *in Methods in Enzymology*, (Wu et al., Eds.), New York, Academic Press, 155:482–501 (1987).

Matthews et al., "Primary amenorrhoea and infertility due to a mutation in the β–subunit of follicle–stimulating hormone," *nature Genetics*, 5:83–86 (Sep. 1993).

Maxson et al., "The Gonadotropin Resistant Ovary Syndrome," *Sem. Reprod. Endocrinol.*, 1(2):147–160 (May, 1983).

Minegish et al., "Cloning and Sequencing of Human FSH Receptor cDNA," *Biochem. Biophys. Res. Comm.*, 175(3):1125–1130 (Mar. 29, 1991).

Myers et al., "Detection of single base changes in DNA: ribonuclease cleavage and denaturing gradient gel electrophoresis," *in Genome Analysis: A Practical Approcah*, Chapter 5, (K.E., Davis, Ed.), Eynsham Oxford, England, IRL Press, pp. 95–139 (1988).

Nevanlinna, H.R., "The Finish population structure," *Hereditas*, 71:195–235 (1972).

Norio, R. "Diseases of Finland and Scandinavia," *in Biocultural Aspects of Disease*, Chapter 12, Academic Press, Inc., pp. 359–415 (1981).

Rannikki et al., "Ontogeny of follicle–stimulating hormone receptor gene expression in the rat testis and ovary," *Mol. Cell Endocrinol.*, 107:199–208 (1995).

Rebar et al., "Clinical Feature of Young Women With Hypergonadotropic Amenorrhea." *Fertility and Sterility*, 53(5):804–810 (May, 1990).

Reindollar et al., "Pubertal Aberrancy: Eriology and Clinical Approach," *J. Reprod. Med.*, 29(6):391–398 Jun. 1984).

Rousseau–Merck et al., "Localization of the human luteinizing hormone/choriogonadotropin receptor gene (LHCGR) to chromosome 2p21," *Cytogenet. Cell. Genet.*, 54:77–79 (1990).

Sambrook et al., *in Molecular Cloning: A Laboratory Manual*, Second Edition Cold Spring Harbor Labratory Press, pp. 13. 7–8, 13.59–64, and 13.73–13.74 (1989).

Sarkar et al., "Access to a Messenger RNA Sequence or Its Protein Product Is Not Limited by Tissue or Species Specificity," *Science*, 244:331–334 (Apr. 21, 1989).

Simpson et al., "Gonadal Dysgenesis in Individuals with Apparently Normal Chromosomal Complements: Tabulation of Cases and Compilation of Genetic Data," *Birth Defects: Original Article Series*, 7(6):215–228 (May, 1971)

Simpson, J.L., "Gonadal Dysgenesis and Sex Chromosome Abnormalities: Phenotypic–Karyotypic Correlations," *in Genetic Mechanisms of Sexual Development*, (J.L.Simpson, Ed.), New York, Academic Press Inc., pp. 365–405 (1979).

Smith et al., "Three Siblings With Premature Gonadal Failure," *Fertility and Sterility*, 32(5):528–530 (Nov., 1979).

Sokka et al., "Ontogeny of gonadotrophin receptors and gonadotrophin–stimulated cyclic AMP production in the neonatal rat ovary," *J. Endocrinol.*, 127:297–303 (1990).

Sprengel et al., "The Testicular receptor for Follicle Stimulating Hormone: Structure and Functional Expression of Cloned cDNA," *Mol. Endocrinol.*, 4(4):525–530 (1990).

Tilly et al., "Hormonal Regulation of Follicle–Stimulating Hormone Receptor Messenger Ribonucleic Acid Levels in cultured Rat Granulosa Cells," *Endocrinol.*, 130(3):1296–1302 (1992).

Van Campenhout et al., "Gonadotropin–Resistant Ovaries in Primary Amenorrhea," *Obstet. Gynecol.*, 40(1):6–12 (Jul., 1972).

Wahlström et al., "Localization of Luteinizing Hormone, Follicle–Stimulating Hormone, Prolactin, and Their Receptors in Human and Rat Testis Using Immunohistochemistry and Radioreceptor Assay," *J. Clin. Endocrinol. Metab.*, 57(4):825–830 (1983).

Weissenbach et al., "A second–generation linkage map of the human genome," *Nature*, 359:794–801 (Oct. 29, 1992).

Yarney et al., "Molecular cloning and expression of the ovine testicular follicle stimulating hormone receptor," *Mol. Cell. Endocrinol.*, 93:219–226 (1993).

Aittomäki et al., "Mutation in the Follicle–Stimulating Hormone Receptor Gene Causes Hereditary Hypergonadotropic Ovarian Failure," *Cell*, 82:959–968 (1995).

Aittomäki, K., "The Genetics of XX Gonadal Dysgenesis, "*Am. J. Hum. Genet.*, 54:844–851 (1994).

Kremer et al., "Male pseudohermaphroditism due to a homozygous missense mutation of the luteinizing hormone receptor gene," *Nature Genetics*, 9:160–164 (1995).

Rousseau–Merck et al., "The Chromosomal Localization of the Human follicle–Stimulating Hormone Receptor Gene (FSHR) on 2p21–p16 Is Similar to That of the Luteinizing Hormone Receptor Gene,"*Genomics*, 15:222–224 (1993).

Rousseau–Merck et al, Genomics 15: 222–224, 1993.

Gromoll et al., J. Of clinical Endocrinology and Metabolism 81: 1367–1370, 1996.

Sankila et al. Human Molecular Genetics 4: 93–98, 1995.

Peschon et al. Molecular Endocrinology 6: 1403–1411, 1992.

Kelton et al. Molecular and Cellular Endocrinology 89: 141–151, 1992.

Whitney et al. Fertility and Sterility 64: 518–523, Sep. 1995.

Gossen et al., PNAS 89: 5547–5551, 1992.

Aasheim et al. Nucleic Acids Research 22: 959–964, 1994.

Karonen et al. Analytical Biochemistry 67: 1–10, 1975.

Gromoll et al. Biochemical and Biophysical Research Communications 188: 1077–1083, 1992.

```
TGTGGAGCTT CTGAGATCTG TGGAGGTTTT TCTCTGCAAA TGCAGGAAGA AATCAGGTGG   60
ATGGATGCAT AATTATGGCC CTGCTCCTGG TCTCTTTGCT GGCATTCCTG AGCTTGGGCT  120
CAGGATGTCA TCATCGGATC TGTCACTGCT CTAACAGGGT TTTTCTCTGC CAAGAGAGCA  180
AGGTGACAGA GATTCCTTCT GACCTCCCGA GGAATGCCAT TGAACTGAGG TTTGTCCTCA  240
CCAAGCTTCG AGTCATCCAA AAAGGTGCAT TTTCAGGATT TGGGGACCTG GAGAAAATAG  300
AGATCTCTCA GAATGATGTC TTGGAGGTGA TAGAGGCAGA TGTGTTCTCC AACCTTCCCA  360
AATTACATGA AATTAGAATT GAAAAGGCCA ACAACCTGCT CTACATCAAC CCTGAGGCCT  420
TCCAGAACCT TCCCAACCTT CAATATCTGT TAATATCCAA CACAGGTATT AAGCACCTTC  480
CAGATGTTCA CAAGATTCAT TCTCTCCAAA AAGTTTTACT TGACATTCAA GATAACATAA  540
```

FIG. 8A

```
ACATCCACAC AATTGAAAGA AATTCTTTCG TGGGGCTGAG CTTTGAAAGT GTGATTCTAT    600
GGCTGAATAA GAATGGGATT CAAGAAATAC ACAACTGTGC ATTCAATGGA ACCCAACTAG    660
ATGAGCTGAA TCTAAGCGAT AATAATAATT TAGAAGAATT GCCTAATGAT GTTTTCCACG    720
GAGCCTCTGG ACCAGTCATT CTAGATATTT CAAGAACAAG GATCCATTCC CTGCCTAGCT    780
ATGGCTTAGA AAATCTTAAG AAGCTGAGGG CCAGGTCGAC AAGCCAGCCT CACCTATCCC    840
CTACTCTGGA AAAGCTTGTC GCCCTCATGG AAGCCAGCCT CACCTATCCC AGCCATTGCT    900
GTGCCTTTGC AAACTGGAGA CGGCAAATCT CTGAGCTTCA TCCAATTTGC AACAAATCTA    960
TTTTAAGGCA AGAAGTTGAT TATATGACTC AGACTAGGGG TCAGAGATCC TCTCTGGCAG   1020
AAGACAATGA GTCCAGCTAC AGCAGAGGAT TTGACATGAC GTACACTGAG TTTGACTATG   1080
```

FIG. 8B

```
ACTTATGCAA TGAAGTGGTT GACGTGACCT GCTCCCCTAA GCCAGATGCA TTCAACCCAT    1140
GTGAAGATAT CATGGGGTAC AACATCCTCA GAGTCCTGAT ATGGTTTATC AGCATCCTGG    1200
CCATCACTGG GAACATCATA GTGCTAGTGA TCCTAACTAC CAGCCAATAT AAACTCACAG    1260
TCCCCAGGTT CCTTATGTGC AACCTGGCCT TTGCTGATCT CTGCATTGGA ATCTACCTGC    1320
TGCTCATTGC ATCAGTTGAT ATCCATACCA AGAGCCAATA TCACAACTAT GCCATTGACT    1380
GGCAAACTGG GGCAGGCTGT GATGCTGCTG GCTTTTTCAC TGTCTTTGCC AGTGAGCTGT    1440
CAGTCTACAC TCTGACAGCT ATCACCTTGG AAAGATGGCA TACCATCACG CATGCCATGC    1500
AGCTGGGACTG CAAGGTGCAG CTCCGCCATG CTGCCAGTGT CATGGTGATG GGCTGGATTT    1560
TGCTTTTTGC AGCTGCCCTC TTTCCCATCT TTGGCATCAG CAGCTACATG AAGGTGAGCA    1620
```

FIG. 8C

```
TCTGCCTGCC CATGGATATT GACAGCCCTT TGTCACAGCT GTATGTCATG TCCCTCCTTG    1680
TGCTCAATGT CCTGGCCTTT GTGGTCATCT GTGGCTGCTA TATCCACATC TACCTCACAG    1740
TGCGGAACCC CAACATGTG TCCTCCTCTA GTGACACCAG GATCGGCCAAG CGCATGGCCA    1800
TGCTCATCTT CACTGACTTC CTCTGCATGG CACCCATTTC TTTCTTTGCC ATTTCTGCCT    1860
CCCTCAAGGT GCCCCTCATC ACTGTGTCCA CCCTTCCTCT ATGCCATCTT TACCAAAAAC    1920
CCATCAACTC CTGTGCCAAC TTGTCTGAGC AAGTGTGGCT GCTATGAAAT GCAAGCCCAA    1980
ATTTCTTCAT TCTGCTGAGC AAGTGTGGCT GCTATGAAAT GCAAGCCCAA ATTTATAGGA    2040
CAGAAACTTC ATCCACTGTC CACAACACCC ATCCAAGGAA TGGCCACTGC TCTTCAGCTC    2100
CCAGAGTCAC CAATGGTTCC ACTTACATAC TTGTCCCTCT AAGTCATTTA GCCCAAAACT    2160
AAAACACAAT GTGAAAATG                                                 2179
```

FIG. 8D

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 2179 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TGTGGAGCTT   CTGAGATCTG   TGGAGGTTTT   TCTCTGCAAA   TGCAGGAAGA   AATCAGGTGG       60
ATGGATGCAT   AATTATGGCC   CTGCTCCTGG   TCTCTTTGCT   GGCATTCCTG   AGCTTGGGCT      120
CAGGATGTCA   TCATCGGATC   TGTCACTGCT   CTAACAGGGT   TTTTCTCTGC   CAAGAGAGCA      180
AGGTGACAGA   GATTCCTTCT   GACCTCCCGA   GGAATGCCAT   TGAACTGAGG   TTTGTCCTCA      240
CCAAGCTTCG   AGTCATCCAA   AAAGGTGCAT   TTTCAGGATT   TGGGGACCTG   GAGAAAATAG      300
AGATCTCTCA   GAATGATGTC   TTGGAGGTGA   TAGAGGCAGA   TGTGTTCTCC   AACCTTCCCA      360
AATTACATGA   AATTAGAATT   GAAAAGGCCA   ACAACCTGCT   CTACATCAAC   CCTGAGGCCT      420
TCCAGAACCT   TCCCAACCTT   CAATATCTGT   TAATATCCAA   CACAGGTATT   AAGCACCTTC      480
CAGATGTTCA   CAAGATTCAT   TCTCTCCAAA   AAGTTTTACT   TGACATTCAA   GATAACATAA      540
ACATCCACAC   AATTGAAAGA   AATTCTTTCG   TGGGGCTGAG   CTTTGAAAGT   GTGATTCTAT      600
GGCTGAATAA   GAATGGGATT   CAAGAAATAC   ACAACTGTGC   ATTCAATGGA   ACCCAACTAG      660
ATGAGCTGAA   TCTAAGCGAT   AATAATAATT   TAGAAGAATT   GCCTAATGAT   GTTTTCCACG      720
GAGCCTCTGG   ACCAGTCATT   CTAGATATTT   CAAGAACAAG   GATCCATTCC   CTGCCTAGCT      780
ATGGCTTAGA   AAATCTTAAG   AAGCTGAGGG   CCAGGTCGAC   TTACAACTTA   AAAAAGCTGC      840
CTACTCTGGA   AAAGCTTGTC   GCCCTCATGG   AAGCCAGCCT   CACCTATCCC   AGCCATTGCT      900
GTGCCTTTGC   AAACTGGAGA   CGGCAAATCT   CTGAGCTTCA   TCCAATTTGC   AACAAATCTA      960
TTTTAAGGCA   AGAAGTTGAT   TATATGACTC   AGACTAGGGG   TCAGAGATCC   TCTCTGGCAG     1020
```

| | | | | | | |
|---|---|---|---|---|---|---|
| AAGACAATGA | GTCCAGCTAC | AGCAGAGGAT | TTGACATGAC | GTACACTGAG | TTTGACTATG | 1080 |
| ACTTATGCAA | TGAAGTGGTT | GACGTGACCT | GCTCCCTAA | GCCAGATGCA | TTCAACCCAT | 1140 |
| GTGAAGATAT | CATGGGGTAC | AACATCCTCA | GAGTCCTGAT | ATGGTTTATC | AGCATCCTGG | 1200 |
| CCATCACTGG | GAACATCATA | GTGCTAGTGA | TCCTAACTAC | CAGCCAATAT | AAACTCACAG | 1260 |
| TCCCCAGGTT | CCTTATGTGC | AACCTGGCCT | TTGCTGATCT | CTGCATTGGA | ATCTACCTGC | 1320 |
| TGCTCATTGC | ATCAGTTGAT | ATCCATACCA | AGAGCCAATA | TCACAACTAT | GCCATTGACT | 1380 |
| GGCAAACTGG | GGCAGGCTGT | GATGCTGCTG | GCTTTTCAC | TGTCTTTGCC | AGTGAGCTGT | 1440 |
| CAGTCTACAC | TCTGACAGCT | ATCACCTTGG | AAAGATGGCA | TACCATCACG | CATGCCATGC | 1500 |
| AGCTGGACTG | CAAGGTGCAG | CTCCGCCATG | CTGCCAGTGT | CATGGTGATG | GGCTGGATTT | 1560 |
| TTGCTTTTGC | AGCTGCCCTC | TTTCCCATCT | TTGGCATCAG | CAGCTACATG | AAGGTGAGCA | 1620 |
| TCTGCCTGCC | CATGGATATT | GACAGCCCTT | TGTCACAGCT | GTATGTCATG | TCCCTCCTTG | 1680 |
| TGCTCAATGT | CCTGGCCTTT | GTGGTCATCT | GTGGCTGCTA | TATCCACATC | TACCTCACAG | 1740 |
| TGCGGAACCC | CAACATCGTG | TCCTCCTCTA | GTGACACCAG | GATCGCCAAG | CGCATGGCCA | 1800 |
| TGCTCATCTT | CACTGACTTC | CTCTGCATGG | CACCCATTTC | TTTCTTTGCC | ATTTCTGCCT | 1860 |
| CCCTCAAGGT | GCCCCTCATC | ACTGTGTCCA | AAGCAAAGAT | TCTGCTGGTT | CTGTTTCACC | 1920 |
| CCATCAACTC | CTGTGCCAAC | CCCTTCCTCT | ATGCCATCTT | TACCAAAAAC | TTTCGCAGAG | 1980 |
| ATTTCTTCAT | TCTGCTGAGC | AAGTGTGGCT | GCTATGAAAT | GCAAGCCCAA | ATTTATAGGA | 2040 |
| CAGAAACTTC | ATCCACTGTC | CACAACACCC | ATCAAGGAA | TGGCCACTGC | TCTTCAGCTC | 2100 |
| CCAGAGTCAC | CAATGGTTCC | ACTTACATAC | TTGTCCCTCT | AAGTCATTTA | GCCCAAAACT | 2160 |
| AAAACACAAT | GTGAAAATG | | | | | 2179 |

( 2 ) INFORMATION FOR SEQ ID NO:2:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| CGCCCGCCGC | GCCCCGCGCC | CGGCCCGCCG | CCCCCGCCCG | GACTTATGCA | ATGAAGTGGT | 60 |
| TG | | | | | | 62 |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| | |
|---|---|
| GTGAAAAAGC CAGCAGCATC | 20 |

( 2 ) INFORMATION FOR SEQ ID NO:4:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CGCCCGCCGC GCCCCGCGCC CGGCCCGCCG CCCCCGCCCG ATTGACTGGC AAACTGGGG        59

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AGAGGAGGAC ACGATGTTGG        20

( 2 ) INFORMATION FOR SEQ ID NO:6:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CGCCCGCCGC GCCCCGCGCC CGGCCCGCCG CCCCCGCCCG GGCTGCTATA TCCACATCTA        60

CC        62

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CAGAACCAGC AGAATCTTTG C        21

( 2 ) INFORMATION FOR SEQ ID NO:8:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CGCCCGCCGC GCCCCGCGCC CGGCCCGCCG CCCCCGCCCG CTTTCTTTGC CATTTCTGCC        60

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA (x i) SEQUENCE DESCRIPTION: SEQ ID NO:9:

CAAAGGCAAG GACTGAATTA TC 22

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:10:

AGCAAAGATT CTGCTGGTTC 20

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:11:

TAGTTTTGGG CTAAATGACT TAGAGGG 27

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:12:

CCTGCTCCTG GTCTCTTTGC TG 22

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:13:

AGAAATTCTT TCGTGGGGCT 20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:14:

GTTTGCAAAG GCACAGCAAT 20

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GTTATTTCAG ATGGCTGAAT AAG          23

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCTCATCTAG TTGGGTTC          18

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GAGTGCACCA TGGGCGGTGT GAAAT          25

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GGGATTCAAG AAATACACAA CTGTGTATTC AATGGAACCC          40

METHOD FOR DIAGNOSIS OF OVARIAN DYSGENESIS

FIELD OF THE INVENTION

The present invention relates to methods for the detection of hereditary ovarian dysgenesis.

BACKGROUND OF THE INVENTION

Normal gonadal function depends upon the integrity of the pituitary-gonadal axis. In females, regulatory control of the ovary is primarily accomplished by the pituitary gonadotropins, follicle-stimulating hormone (FSH) and luteinizing hormone (LH). At birth, development of the ovarian follicles is normally arrested until pituitary gonadotropin stimulation at puberty causes follicular maturation. Either the failure of the pituitary to secrete sufficient amounts of FSH and/or LH or the failure of the ovary to respond to gonadotropin stimulation results in hypogonadism. In females, such a condition may be characterized by the development of anatomically normal internal and external genitalia, variably developed secondary sexual characteristics, and amenorrhea. Failure of the ovaries to respond appropriately to FSH and/or LH stimulation results in poorly-developed (streak) ovaries and increased circulating levels of the hormone(s) to which the ovary is not responding. Such a condition is referred to as ovarian dysgenesis. That disease is one of a group of diseases characterized by hypogonadism which are often referred to generally as hypergonadotropic hypogonadisms. Many such diseases are due to mutations in the sex chromosomes. However, ovarian dysgenesis in females with an XX karyotype is rare and may be due to an autosomal recessive mutation. Simpson, et al., *Birth Defects: Original Article Series,* 7: 215–228 (1971); Aittomkäki, *Am. J. Genet.,* 54: 844–851 (1994).

Also of interest to the present invention are the receptors for FSH and LH. Each of those receptors is a member of a family of receptors which are coupled to GTP-binding proteins (G-proteins) in order to effect intracellular signalling. Other members of this family include certain adrenergic receptors, muscarinic cholinergic receptors, vasopressin receptors, and angiotensin receptors. Most receptors in this family comprise three distinct domains, an extracellular domain, a transmembrane domain typically having seven membrane-spanning regions with six intervening loops, and an intracellular carboxy-terminal domain. The transmembrane domain is highly conserved in G-protein coupled receptors. However, LH and FSH are distinguished from other members of the family by their relatively large extracellular ligand binding domain.

While ovarian dysgenesis has been studied at the hormonal level, no causative mutation has been proposed and no screening method for diagnosis of ovarian dysgenesis has been available. Accordingly, there is a need in the art for an accurate, reliable method for diagnosing ovarian dysgenesis as provided by the present invention.

SUMMARY OF THE INVENTION

Methods according to the invention are useful for diagnosing ovarian dysgenesis and other hypergonadotropic hypogonadisms in female patients. In a preferred embodiment, a method according to the invention comprises the steps of obtaining a cell sample from a female patient, isolating DNA from the cell sample; amplifying a portion of the DNA encoding a receptor for follicle-stimulating hormone; exposing the amplified DNA to the restriction endonuclease, BsmI or a restriction endonuclease having a recognition sequence which overlaps that of BsmI or which recognizes the same cleavage site as BsmI, including isoschizomers of BsmI; and diagnosing ovarian dysgenesis as the appearance of four products of BsmI digestion. The enzyme BsmI recognizes the sequence GCATTC and cleaves between G and C. Restriction endonucleases that recognize sequences which overlap that of BsmI, such as SacIII or SstIII, may also be used since those enzymes also cut an intact BsmI site.

Also in a preferred embodiment of the invention, a method for diagnosing ovarian dysgenesis is presented, comprising the steps of obtaining a cell sample from a female patient; isolating DNA from the cell sample; amplifying a portion of the DNA encoding exon 7 of the follicle-stimulating hormone receptor; exposing the amplified DNA to BsmI or another restriction endonuclease which recognizes the BsmI site; and diagnosing ovarian dysgenesis as the presence of a single fragment upon digestion.

In another embodiment of the invention, a method for diagnosing ovarian dysgenesis comprises the steps of obtaining a cell sample from a female patient; isolating DNA from the cell sample; amplifying a portion of the DNA encoding follicle-stimulating hormone receptor or exon 7 of follicle-stimulating hormone receptor; comparing the sequence of the isolated DNA with the wild-type sequence shown in SEQ ID NO: 1; and diagnosing ovarian dysgenesis on the basis of differences in the sequences of the isolated DNA and the sequence shown in SEQ ID NO: 1. Numerous mutations may be causative of ovarian dysgenesis. Thus, a number of differences between the FSH receptor-encoding DNA obtained from the patient and the wild-type sequence shown in SEQ ID NO: 1 are indicative of ovarian dysgenesis, especially in patients having other symptoms of the disease.

In a preferred embodiment of the invention, a change in the nucleotide sequence encoding an FSH receptor at position 646 of the FSH receptor coding sequence shown in SEQ ID NO: 1, wherein a cytosine is changed to another nucleotide, typically a thymrine, is used in the diagnosis of ovarian dysgenesis according to the invention.

Additional aspects of the invention will become apparent upon consideration of the following detailed description thereof.

DESCRIPTION OF THE DRAWINGS

FIGS. 8A, and 8B, 8C and 8D are the nucleotide sequence of the FSH receptor (SEQ ID NO:1) showing BsmI sites in bold.

DETAILED DESCRIPTION OF THE INVENTION

The present invention provides methods for the diagnosis of diseases characterized by ovarian dysfunction. In particular, methods of the invention are useful in the diagnosis of ovarian dysgenesis in females. Diagnostic methods according to the invention may be used at any time in the life of the patient, even prior to the onset of symptoms, such as the failure of normal onset of menstruation at puberty. Methods of the invention are primarily based upon the discovery that a mutation in the coding sequence of the gene for the follicle-stimulating hormone receptor accounts for the inability of FSH to bind and generate signal transduction at its receptor.

In the normal genotype for the follicle-stimulating hormone receptor, there exists four BsmI sites (5'NGCATTC3') as shown in FIGS. 8A and 8B, 8C, and 8D. In ovarian dysgenesis, the BsmI site at nucleotides 638–644 (exon 7) of the sequence shown in SEQ ID NO: 1 is mutated at position 640 such that a thymine is substituted for a cytosine, resulting in the sequence, 5'NGTATTC3'. Thus, digestion of DNA encoding a wild-type FSH receptor with BsmI normally produces five fragments (due to cuts made at all four BsmI sites in a linear DNA). However, a thymine-to-cytosine mutation at position 640 results in a mutated DNA that produces only four fragments upon BsmI digestion. As shown below, mutation at position 640 is uniquely associated with ovarian dysgenesis; whereas no mutation at any of the other three BsmI sites in the FSH receptor DNA has been found in patients suffering from that disease. Accordingly, BsmI digestion and subsequent observation of the products produced is useful as a diagnostic method or a screening method for ovarian dysgenesis. As detailed below, the region of exon 7, or a portion thereof, of the FSH receptor coding sequence may also be isolated and exposed to BsmI. Exon 7 contains a unique BsmI site which, if mutated, will produce no BsmI digestion products, thereby enabling diagnosis of ovarian dysgenesis.

Figure 1:
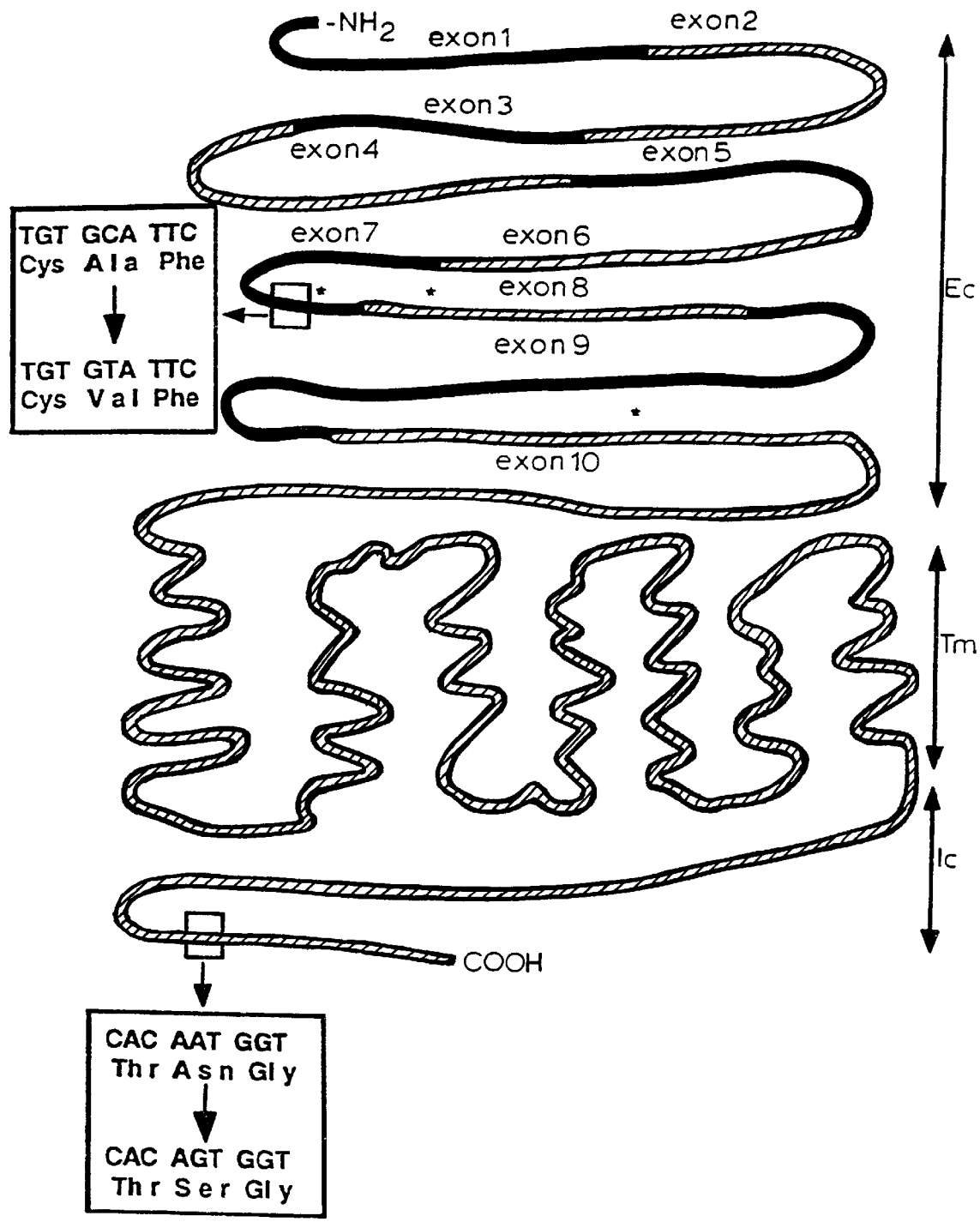
FIG. 1 is a schematic representation of the human FSH receptor showing the Ala to Val and Asn to Ser transitions.

The gene encoding the FSH receptor has been mapped to human chromosome 2p16–21. Rousseau-Merck, et al., *Genomics*, 15: 222–224 (1993). That gene comprises 10 exons which encode the three protein domains referred to above. The FSH receptor coding sequence is shown in SEQ ID NO: 1 and in FIGS. 8A, 8B, 8C, and 8D and is available in the Genbank database as Accession No., S59900. FIG. 1 shows a schematic of the FSH receptor showing the regions encoded by the 10 exons.

The following examples illustrate preferred means for diagnosis of ovarian dysgenesis.

EXAMPLE 1

Figure 2:
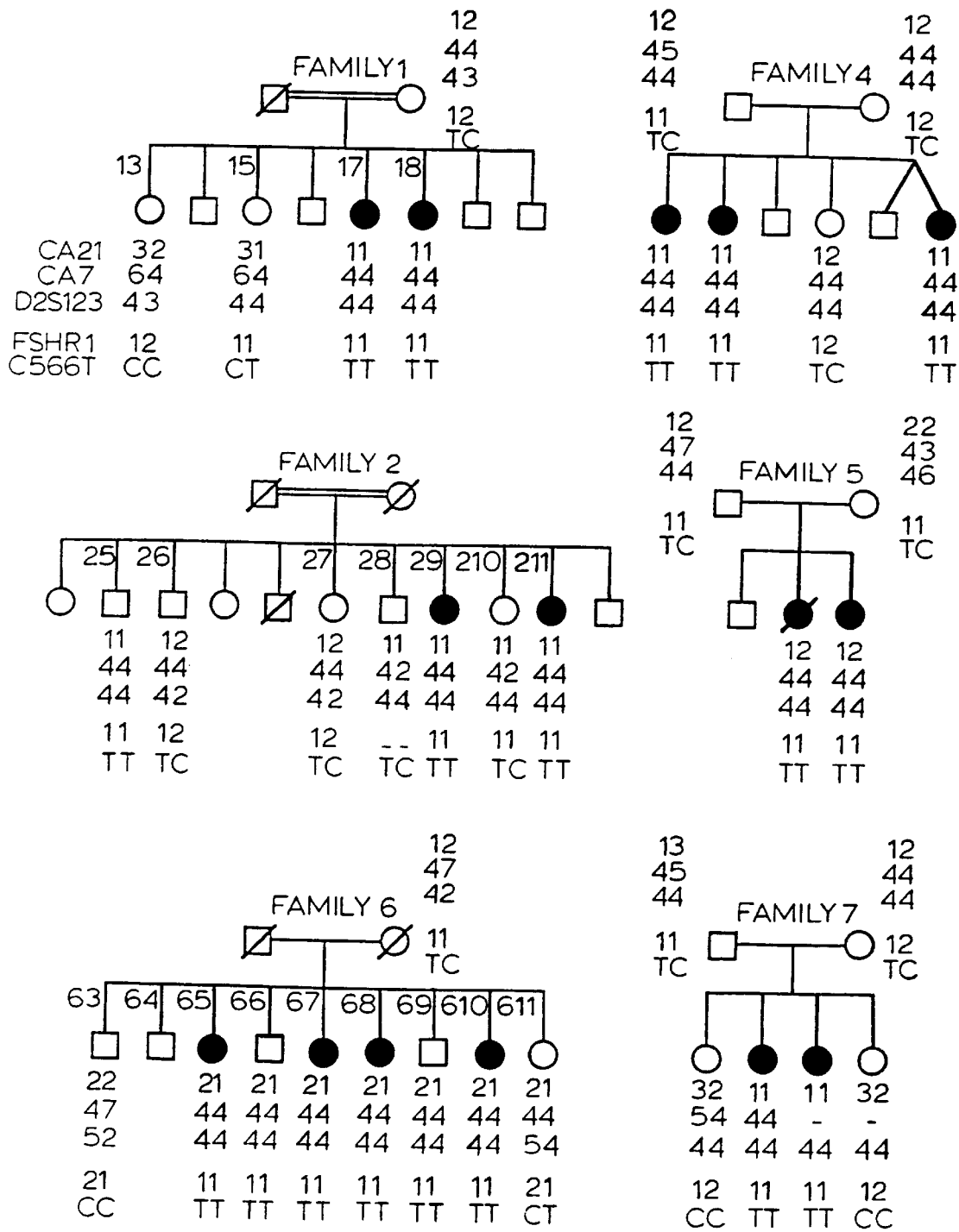
FIG. 2 shows a pedigree of families used in studies of ovarian dysgenesis inheritance patterns.
Figure 3A:
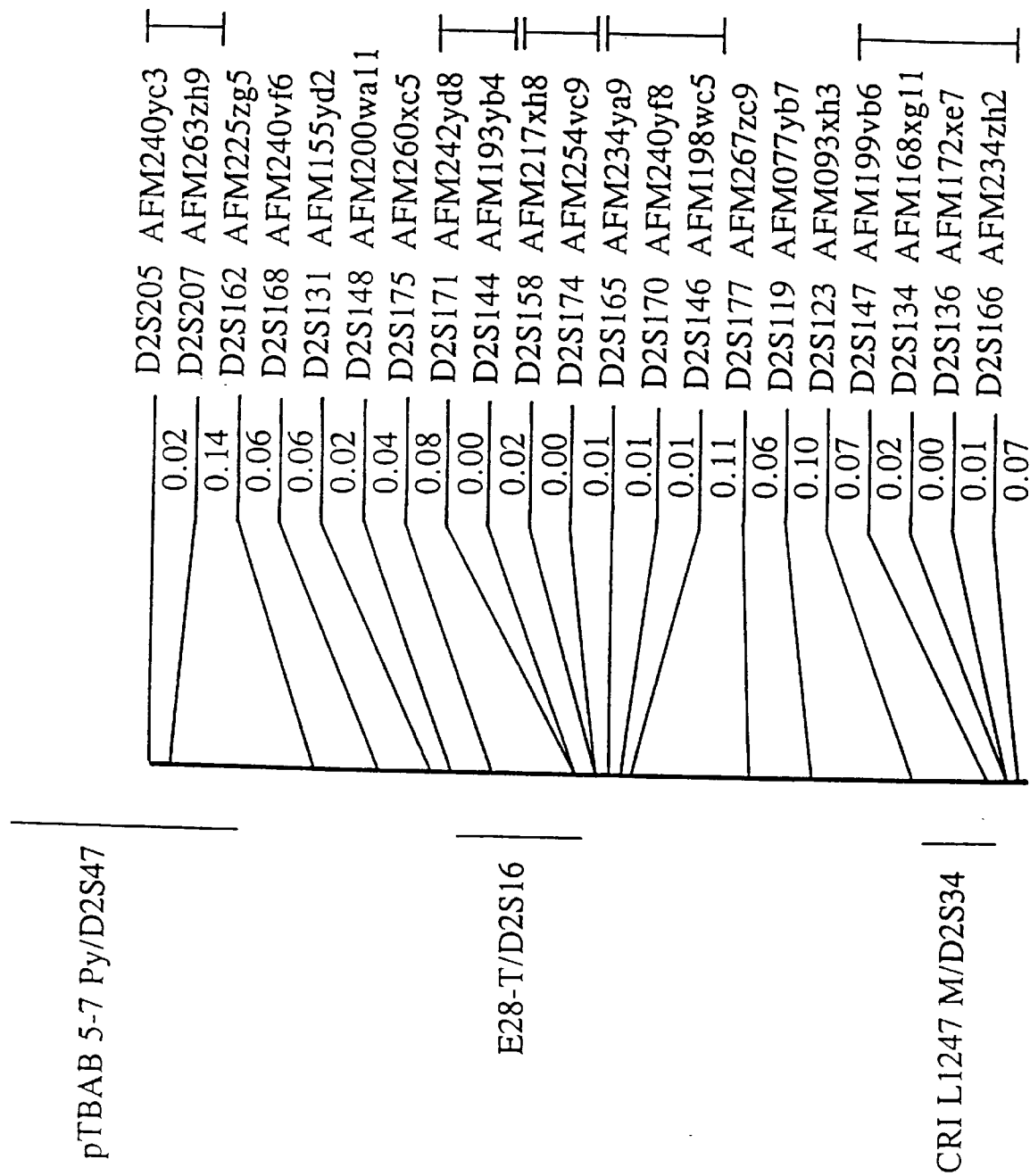
FIG. 3A, FIG. 3B, FIG. 3C and FIG. 3D collectively show is a map of microsatellite markers on human chromosome 2.
Figure 3B:
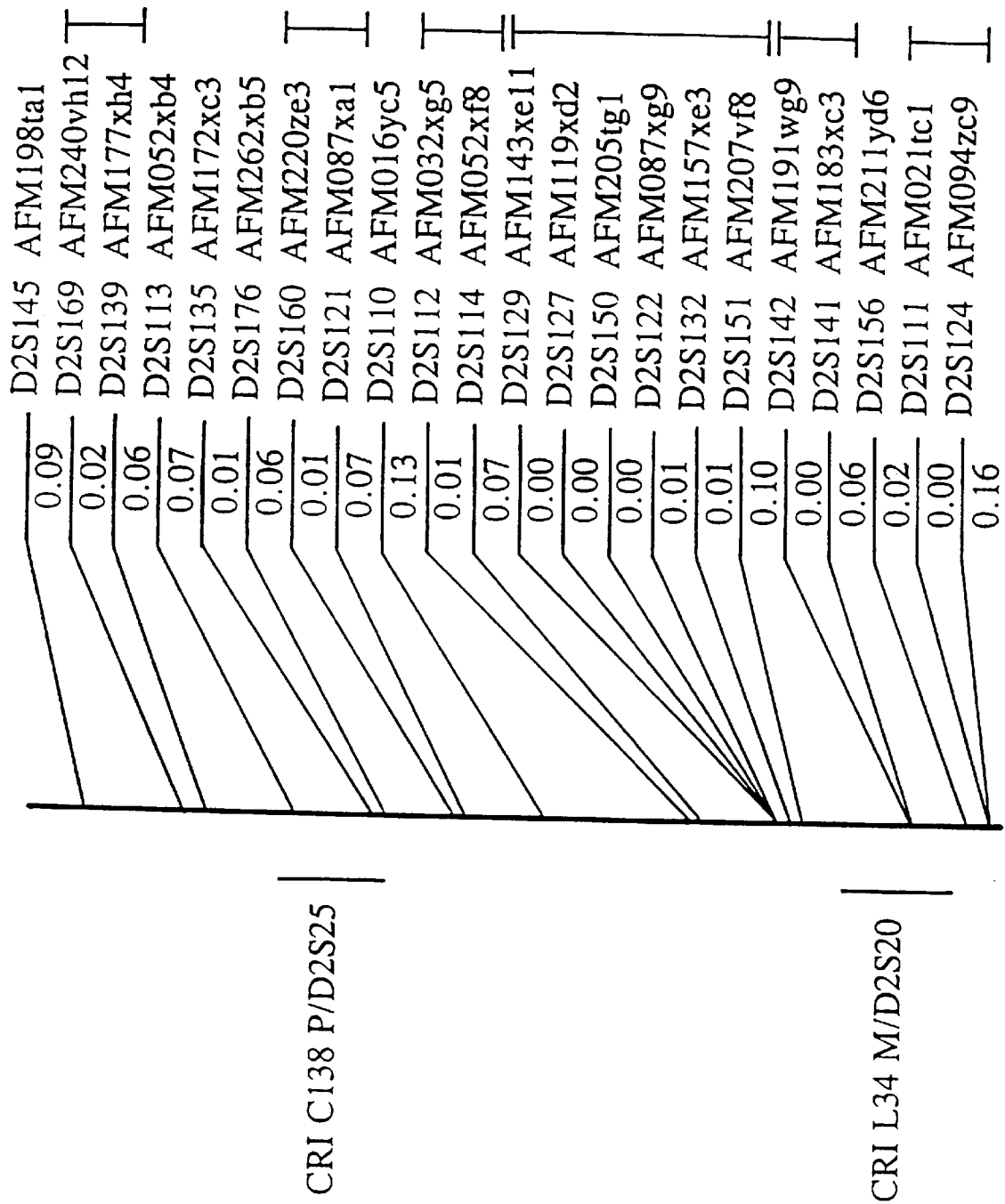
Figure 3C:
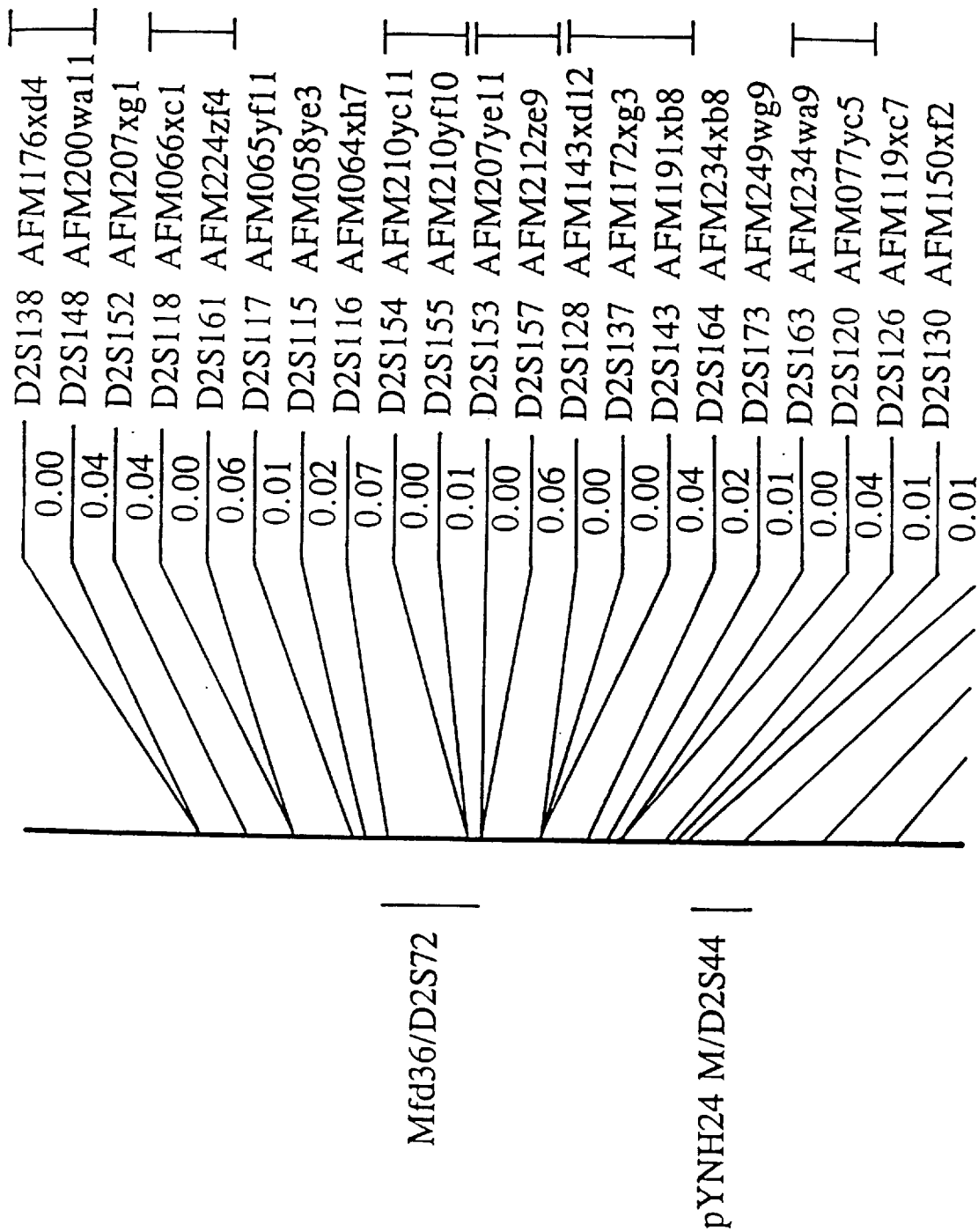
Figure 3D:
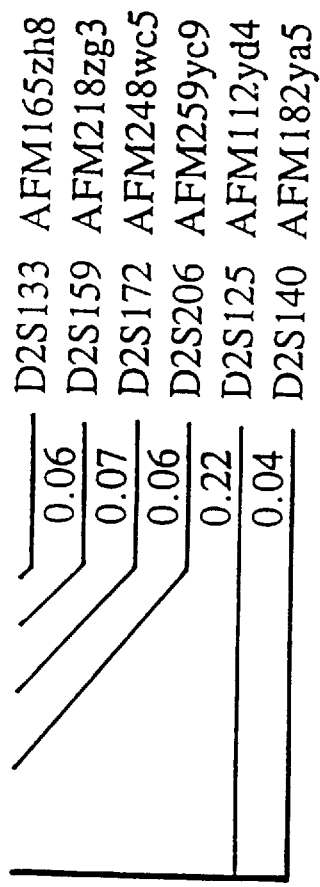

Venous blood samples were obtained from 37 individuals, each belonging to one of 6 families having at least two females with symptoms of ovarian dysgenesis. Total DNA was isolated from fresh white blood cells or lymphoblastoid cell lines established from the samples. The method of Chomczynski, et al., *Anal. Biochem.*, 162: 156–159 (1987), incorporated by reference herein, was used to isolate RNA from the samples. A pedigree showing inheritance patterns in individuals used to isolate the ovarian dysgenesis locus is shown in FIG. 2.

Linkage was investigated using Généthon microsatellite markers as reported in Weissenbach, et al., *Nature*, 359: 794–801 (1992), incorporated by reference herein. A linkage map for chromosome 2 is provided in FIG. 3A, FIG. 3B, FIG 3C, and FIG. 3D. Forty-seven markers were chosen at approximately 20 cM intervals. Pairwise linkage analyses were carried out using the MLINK subprogram of the LINKAGE program package reported in Lathrop, et al., *Proc. Nat'l. Acad. Sci.* (USA), 81: 3443–3446 (1984), incorporated herein by reference. The disease allele frequency was set to 0.01 and lod scores were computed under a model of equilibrium between the disease locus and each marker locus, assuming a recessive mode of inheritance with full penetrance in females. A lod score is defined as the $\log_{10}$ of the ratio of the probability that the data obtained would have arisen from unlinked loci and represents a criterion for assigning a given restriction fragment length polymorphism to a particular linkage group. Linkage was confirmed using the G2113A transition located in exon 10 of the FSH receptor gene as a polymorphic marker (see below). Amplification was accomplished using PCR according to the method of Sankila, et al., *Hum. Mol. Genet.*, 4: 93–98 (1995), incorporated by reference herein.

Preliminary evidence of linkage of the ovarian dysgenesis phenotype was noted for markers D2S134 and D2S177 on chromosome 2. Linkage was confirmed using markers D2S119 and D2S123, each of which is located between D2S134 and D2S177. Markers D2S119 and D2S123 define an approximately 12 cM region of chromosome 2. That region was further studied using markers D2S391, D2S288, CA21 and CA7, each of which is located in the 12 cM region defined above, and linkage of the ovarian dysgenesis locus to this region of chromosome 2 was confirmed.

Pairwise linkage analyses produced 46 potentially informative meioses, of which 30 were from affected females. The lod scores obtained from those meioses revealed no recombinations between the markers and the ovarian dysgenesis locus as evidenced by phenotype. The highest lod score, $Z_{max}=4.71$, was obtained for marker D2S391, while two other marker loci, D2S288 and CA21, provided lod scores exceeding the limit of proven linkage ($Z \geq 3.0$). The region in which linkage of the ovarian dysgenesis phenotype exists was, therefore, isolated to the 2p region of chromosome 2 based upon the above linkage analysis. That region of chromosome 2 is the region which contains the genes encoding the receptors for follicle-stimulating hormone and luteinizing hormone. Thus, it was hypothesized that a non-lethal mutation in one of these two genes was responsible for ovarian dysgenesis. On the basis that an LH receptor mutation would also cause severe hypogonadism in males and no males were affected in the pedigrees producing affected females, the LH receptor gene was considered unlikely as a site of mutation causing ovarian dysgenesis. Accordingly, the gene encoding the FSH receptor was investigated as a source of the ovarian dysgenesis phenotype.

EXAMPLE 2

As shown in FIG. 1, the FSH receptor gene comprises 10 exons. A systematic analysis was performed to determine the change or changes in that gene which are responsible for expression of the ovarian dysgenesis phenotype.

The large terminal exon of the FSH receptor was screened for mutations using denaturing gradient gel electrophoresis. Exon 10 was amplified with GC clamped primers in four different PCR reactions with overlapping products covering the entire transmembrane and intracellular domains. Pairs of GC clamped primers used in PCR were primer 10f:
5'CGCCCGCCGCGCCCCGCGCCCGGCCCGC-CGCCCCGCCCGGACT TATGCAATGAAGTG-GTTG3' (forward, SEQ ID NO: 2), 10r:

5'GTGAAAAAGCCAGCAGCATC3' (reverse, SEQ ID NO: 3); primer 11f:
5'CGCCCGCCGCGCCCCGCGCCCGGCCCGC-CGCCCCGCCCGATTG ACTGGCAAACTGGGG3' (forward, SEQ ID NO: 4), 11r:
5'AGAGGAGGACACGATGTTGG3' (reverse, SEQ ID NO: 5); primer 12f:
5'CGCCCGCCGCGCCCCGCGCCCGGCCCGC-CGCCCCGCCCGGGCT GCTATATCCACATCTACC3'(forward, SEQ ID NO: 6), 12r:
5'CAGAACCAGCAGAATCTTTGC3' (reverse, SEQ ID NO: 7); and primer
13f:5'CGCCCGCCGCGCCCCGCGCCCGGCCCGCCG-CCCCGCCCGC TTTcTTTGCCATTTCTGCC3' (forward, SEQ ID NO: 8), 13r 5'CAAAGGCAAGGACT-GAATTATC3' (reverse, SEQ ID NO: 9). Each pair of primers was optimized for each fragment with the MELT 87 program described in Lerman, et al., *Methods in Enzymology* (Wu, et al., eds. 1989), incorporated by reference herein. For each PCR run, samples were heated to 94° C. for 4 minutes and put through 34 cycles. For each cycle, denaturation was conducted for 1 minute at 94° C., annealing was conducted for 1 minute at 57° C., 58° C., 57° C., and 54° C. for primers 10, 11, 12, and 13, respectively, and extension was for 30 seconds at 72° C.

A 7% polyacrylamide gel was designed for each fragment with a linear concentration gradient of formamide. Gels were run in an aquarium at a stable temperature of about 60° C. for 16–20 hours in a denaturing gel electrophoresis system, model DGGE2000 (C.B.S. Scientific Co.). Denaturing gradient gel electrophoresis procedures are generally known in the art and are available, for example, in Ausubel, et al. (eds.) *Current Protocols in Molecular Biology*, 2.12, et seq. (1987), incorporated by reference herein.

A sequence polymorphism was detected in the terminal region of exon 10. A 326 bp fragment corresponding to nucleotides 1818 through 2143 of the FSH receptor coding sequence was amplified using primers 14f: 5'AGCAAA-GATTCTGCTGGTTC3' (forward, SEQ ID NO: 10) and 14r: 5'CAAAGGCAAGGACTGAATTATC3' (reverse, SEQ ID NO: 9). The amplified PCR product was sequenced using the dideoxy chain termination method as reported in Molecular Cloning: A Laboratory Manual (Sambrook, et al., eds 1992), incorporated by reference herein. A G-to-A transition was observed in the sequenced product at nucleotide position 2113 (G2113A transition). Position 2113 is in the region encoding the intracellular domain of the FSH receptor and predicts a change from Ser to Asn at amino acid position 680 of the corresponding protein structure. The G2113A transition abolishes a BsrI site, thus enabling BsrI to be used as a screen for the two alleles. The polymorphism at that site was designated FSHR1.

The G2113A transition observed in exon 10 of the FSH receptor coding sequence had previously been identified as a difference between the ovarian and testicular forms of the gene encoding the FSH receptor. Kelton, et al., *Mol. Cell. Endocrinol.*, 89: 141–151 (1992). Denaturing gradient gel electrophoresis analysis of samples obtained from a family having females both with and without ovarian dysgenesis showed that the allelic form of the gene at the G2113A transition had no affect on phenotype. Thus, the allelic variance at position 2113 was not considered to be disease causing. No recombinations between that locus and the disease phenotype were observed, as shown in Table 1.

TABLE 1

| Marker locus | Recombination fraction, φ | | | | | | | 90% support interval |
|---|---|---|---|---|---|---|---|---|
| | 0.00 | 0.001 | 0.01 | 0.05 | 0.10 | 0.20 | 0.30 | |
| D2S119 | 2.41 | 2.41 | 2.35 | 2.12 | 1.82 | 1.20 | 0.62 | 0–0.17 |
| D2S391 | 4.71 | 4.70 | 4.59 | 4.14 | 3.56 | 2.38 | 1.26 | 0–0.09 |
| D2S288 | 3.10 | 3.10 | 3.03 | 2.72 | 2.33 | 1.52 | 0.78 | 0–0.13 |
| CA21 | 4.20 | 4.19 | 4.11 | 3.74 | 3.24 | 2.19 | 1.16 | 0–0.10 |
| CA7 | 2.66 | 2.66 | 2.60 | 2.35 | 2.03 | 1.36 | 0.71 | 0–0.16 |
| D2S123 | 2.68 | 2.67 | 2.62 | 2.39 | 2.08 | 1.44 | 0.79 | 0–0.16 |
| FSHR1 | 2.72 | 2.71 | 2.66 | 2.44 | 2.14 | 1.49 | 0.82 | 0–0.16 |

The FSHR1 locus was, however, used as a marker in the linkage analysis described above. Since the polymorphism in exon 10 was excluded as the source of the ovarian dysgenesis phenotype, the other exons of the FSH receptor were screened.

EXAMPLE 3

Exons 1–5 and 9 were screened by amplifying each with flanking intronic primers and sequencing the PCR product. None of those exons showed a mutation associated with the ovarian dysgenesis phenotype.

Complete sequences for the flanking introns of exons 6, 7, and 8 were not available. However, it was determined that FSH receptor-encoding mRNA could be isolated by using RNA from blood leukocytes as a template. Such a process takes advantage of so-called illegitimate transcription, whereby small amounts of MRNA encoding most tissue-specific proteins are produced by white blood cells. Due to the sensitivity of PCR and since PCR products can be directly sequenced, small amounts of RNA produced by white blood cells were used to amplify the FSH receptor coding region. RNA was isolated from white blood cells and exons 6–9 were amplified by reverse transcription PCR in order to identify mutations by direct sequencing of the PCR products as follows.

Total RNA was isolated from white blood cells or from lymphoblasts. Approximately 0.8 μg RNA was used as a template for first-strand cDNA synthesis and primed for reverse transcription by 40 pmol of primer 15r: 5'TAGTTTTGGGCTAAATGACTTAGAGGG3' (SEQ ID NO: 11). Approximately 1 mM each of dATP, dCTP, dTTP, dGTP and 200 U M-mLv reverse transcriptase were combined in M-mLv reverse transcriptase buffer (Promega, Madison, Wis.) to a final volume 20 μL. Samples were incubated at 42° C. for 1 hour. Samples were then heated to 95° C. for 10 minutes and a 5 μl aliquot of the resulting cDNA product was used as a template for PCR.

The cDNA was amplified in two rounds of PCR using a nesting strategy in order to increase yield and specificity. In the first round of PCR, primer 15r (see above) and primer 16f:
5'CCTGCTCCTGGTCTCTTTGCTG (SEQ ID NO: 12) were used. The reaction was heated for 2 minutes at 94° C. and put through 20 cycles each comprising 1 minute denaturing at 94° C., 1 minute annealing at 58° C. and 2 minutes extension at 73° C. to produce a 2082 bp product. The product contained exons 6–9 and 5 μl was used as a template for amplification of exon 7 using primer 6f: 5'AGAAATTCTTTCGTGGGGCT3' (forward, SEQ ID NO: 13) and 6r: 5'GTTTGCAAAGGCACAGCAAT3' (reverse, SEQ ID NO: 14). The resulting PCR product was a 357 bp fragment.

Figures 4A, 4B, 4C:
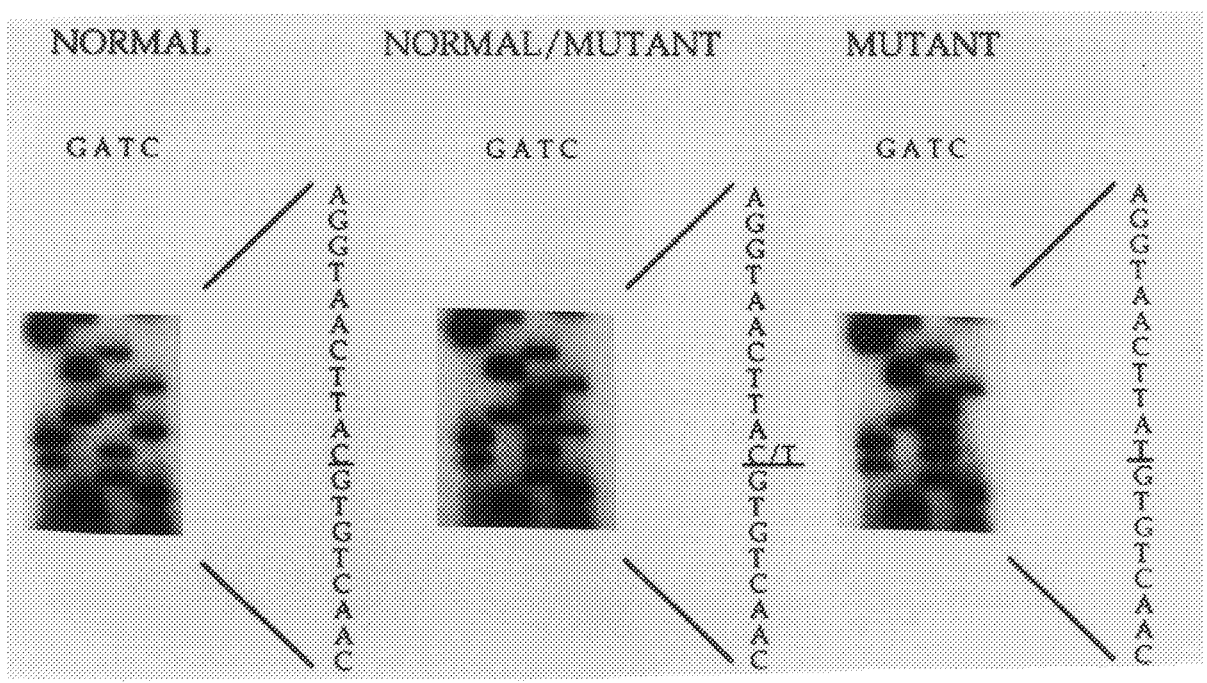
FIG. 4A shows results of gel sequencing analysis of homozygous wild-type individuals at the C640T transition.
FIG. 4B shows results of gel sequencing analysis of heterozygous individuals at the C640T transition.
FIG. 4C shows results of gel sequencing analysis of homozygous mutated individuals at the C640T transition.

The 357 bp product, corresponding to exon 7, was sequenced. Upon inspection of the resulting sequence in a number of patients (both affected and unaffected), it was noticed that all affected individuals were homozygous for a C-to-T transition at nucleotide 640 (C646T transition) of the FSH receptor sequence shown in SEQ ID NO: 1. That change predicts an Ala-to-Val substitution at amino acid position 189 in the corresponding protein primary structure. Gels showing the nucleotide pattern at this locus in homozygous wild-type, heterozygous, and homozygous mutated female genotypes are provided in FIGS. 4A–4C. The C640T transition segregated perfectly with the disease phenotype and all affected individuals were determined to be homozygous recessive for the mutation from cystosine to thymine. The mutation at position, 640 abolishes a BsmI restriction site, thus enabling diagnosis of the disease by digestion, of FSH receptor DNA with BsmI. Thus, it was determined that the C640T transition in exon 7 of the FSH receptor gene is predictive of ovarian dysgenesis in affected individuals.

EXAMPLE 4

Digestion of genomic DNA with BsmI was next used in order to confirm the use of that enzyme in the diagnosis of ovarian dysgenesis.

Genomic DNA isolated from 15 affected and 22 unaffected individuals was amplified by PCR by heating for 12 minutes at 94° C. followed by 30 cycles at 94° C. for 1 minute, 54° C. for 1 minute, and 72° C. for 2 minutes using primers 7f: 5'GTTATTTCAGATGCTGAATAAG3' (SEQ ID NO: 15) and 7r: 5'GCTCATCTAGTTGGGTTC3' (SEQ ID NO: 16). Fifteen microliters of the resulting 78 bp PCR product encompassing the region of exon 7 containing the C640T transition which contains a unique BsmI site in unaffected individuals (there are three additional BsmI sites in the region encoding the FSH receptor, but these are not in exon 7 and are not included in the above-described PCR product), was digested to completion with 20 IU of BsmI (Promega). The product of digestion was fractionated on a 10% nondenaturing polyacrylamide gel and the DNA was visualized with ethidium bromide.

Figure 5:
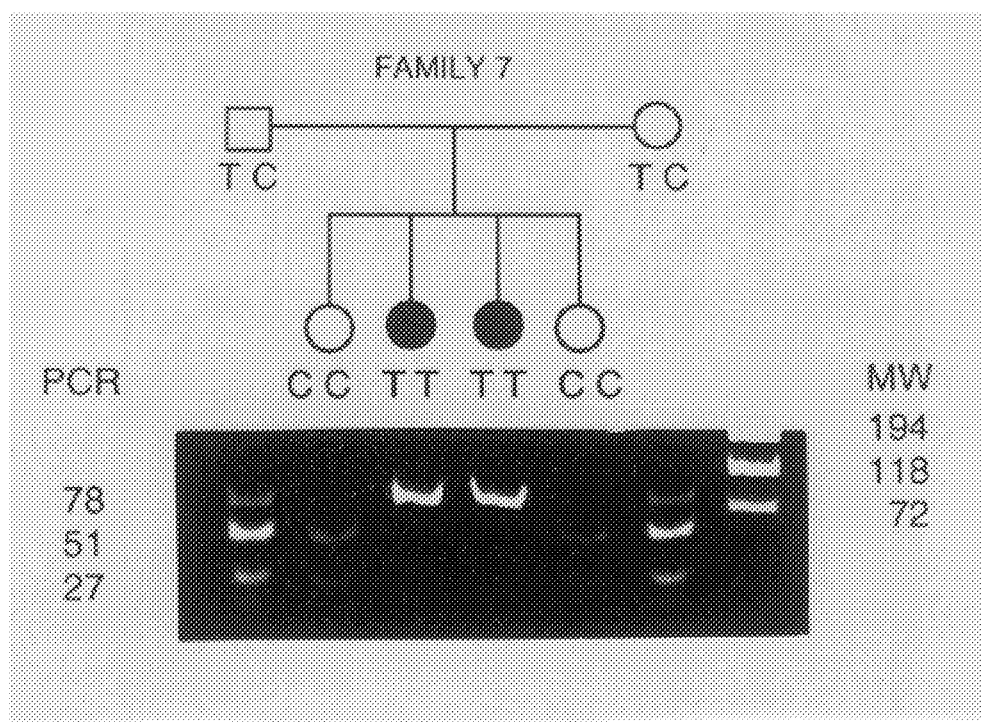
FIG. 5 is a pedigree and gel showing products of digestion of exon 7 with BsmI in normal and mutated individuals.

FIG. 5 shows a typical gel with the corresponding pedigree matched from individual to lane. Darkened circles in the pedigree represent affected females. In unaffected individuals, the PCR product is cleaved into 51 bp and 27 bp fragments by BsmI. However, in affected individuals, only a 78 bp fragment appears in the gel. Heterozygous individuals, such as the parents shown in the pedigree in FIG. 5, show all three fragments (see lanes 1 and 6). Lane 7 represents the molecular weight standards. Thus, BsmI digestion is probative of ovarian dysgenesis by detecting the C640T transition. The pathogenic role of the C639T transition was further confirmed in FSH receptor signalling and binding studies.

EXAMPLE 5

Human FSH receptor-encoding DNA was obtained by reverse transcription PCR using testicular poly (A$^+$) RNA as reported in Gromoll, et al., *Biochem. Biophys. Res. Commun.*, 188:1077–1083 (1992), incorporated by reference herein. The resulting PCR product was subcloned into a pBluescript SR(-) vector (Stratagene). A 5' untranslated region which contained a stop codon was deleted and a Kozak translation initiation sequence was added. The resulting construct comprised 2088 bp of the FSH receptor coding region with a 5-base 5' extension and a 92-base 3' extension. The entire sequence is reported in the Genbank database under accession number X68044, incorporated by reference herein. The FSH receptor coding sequence with 5' and 3' extensions was excised by digestion with SmaI and KpnI and bluntend ligated into a blunted EcoRI site in the pSG5 vector (Stratagene).

A plasmid comprising the mutated receptor (i.e. the C640T allele) was created by site-directed mutagenesis of the wild-type cDNA. Site-directed mutagenesis was accomplished using a Clontech Transformer™ site-directed mutagenesis kit (Clontech, Palo Alto, Calif.) according to the manufacturer's instructions. The selection primer, 5'GAGTGCACCATGGGCGGTGTGAAAT3' (SEQ ID NO: 17), transformed an NdeI site into an NcoI site in the vector. The mutagenesis primer, 5' GGGATTCAAGAAATACACAACTGTGTAT-TCAATGGAACCC3' (SEQ ID NO: 18), accomplishes the C-to-T transition at position 640. Plasmid sequences were verified by restriction digestion and sequencing.

An MSC-1 cell line was used for transfection. That cell line was derived from a transgenic mouse Sertoli cell tumor generated by expressing the SV40 virus T-antigen under the control of the anti-muellerian hormone promoter reported in Peschon, et al., *Mol. Endocrinol.*, 6:1403–1411 (1992), incorporated by reference herein. Despite their origin in Sertoli cells, MSC-1 cells do not express endogenous FSH receptor. MSC-1 cells in exponential growth phase were transiently transfected with either the wild-type or mutated FSH receptor-containing plasmids described above. Transfection was accomplished in DMEM/F12 (1:1) medium using lipofection (Gibco Life Technologies, Inc.) according to the manufacturer's instruction. A mock transfection with buffer was run as a control. Transfection efficiency was maintained by cotransfection with a luciferase-expressing pCmv-luci plasmid as reported in Gossen, et al., *Proc. Nat'l. Acad. Sci. (USA)*, 89:5547–5551 (1992). Transfected cells were cultured in 2 cm culture plates.

Seventy-two hours after transfection, cells were exposed to one of 2, 10, 50, 100, or 200 IU/L of recombinant human FSH (rhFSH, Org 32489, approximately 10,000 IU/mg, Organon International BV). A control (vehicle only) was also run. After 3 hours, cells and media were removed from the culture plates and divided into two equal aliquots. One of the aliquots was diluted 1:1 with 2 mM theophylline, heated for 5 minutes at 100° C., spun for 5 minutes at 1500 g; and used to measure cAMP activity as described in Harper, et al., *J. Cycl. Nucleotide Res.*, 1:207–218 (1975), incorporated by reference herein.

Figure 6:
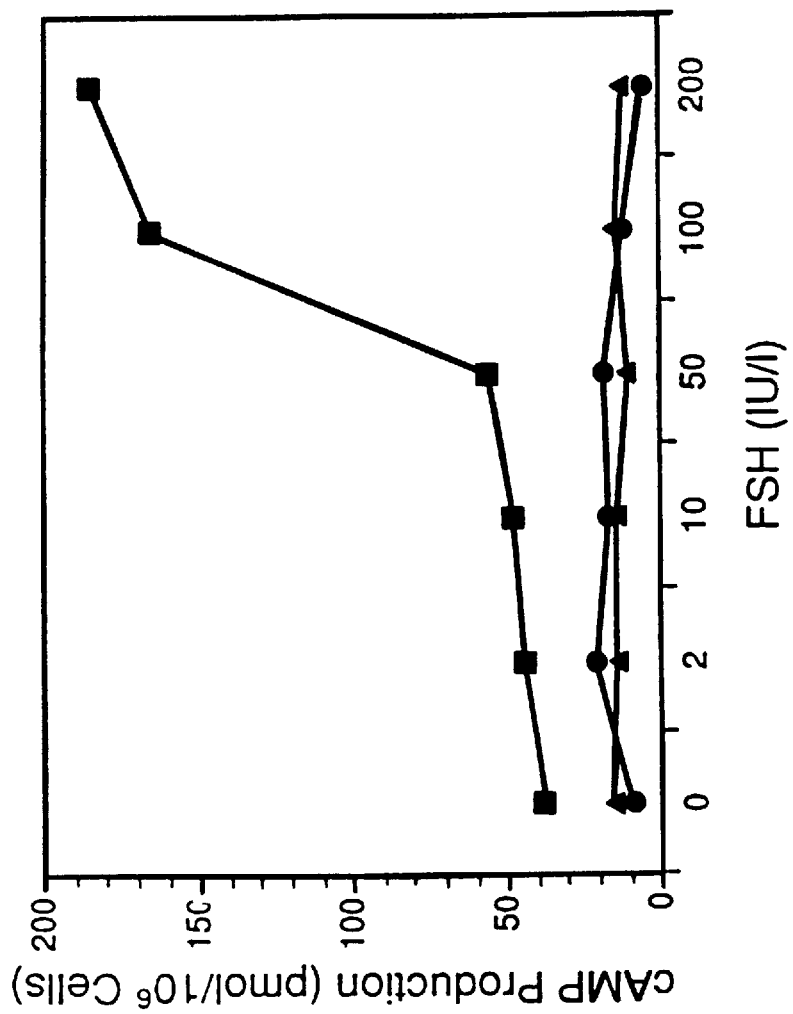
FIG. 6 is a graph showing results of FSH-induced cAMP production by MSC01 cells transfected with wild-type or mutant FSH receptor-encoding DNA.

Stimulation with rhFSH of MSC-1 cells transfected with wild-type FSH receptor DNA produced a 3–4 fold dose-dependent stimulation of cAMP as shown in FIG. 6. The $ED_{50}$ of stimulation was approximately 75 IU/L. In contrast, cells transfected with DNA comprising the C640T allele or with only pCmv-luci produced only negligible increases in cAMP activity, indicating that such cells are not stimulated by FSH. The results are shown in FIG. 6, wherein squares denote the wild type allele, circles denote the mutant allele, and triangles represent mock transfections. Each data point in FIG. 6 represents the mean of results in three identical experiments.

The foregoing results show that the ovarian dysgenesis allele (i.e. that with a substitution of T for C at position 640) results in the expression of a receptor which is unable to produce a signal upon stimulation by FSH.

EXAMPLE 6

MSC-1 cells which had been transfected with either mutant or wild-type FSH receptor plasmids were next used in FSH binding studies performed 48 hours after transfection. Cells were recovered and reconstituted to a concentration of 2×10⁶ cells/ml in buffer. The rhFSH described above was radiolabelled with $^{125}$I iodine using the solid-phase lactoperoxidase method of Karonen, et al., *Anal. Biochem.*, 67:1–10 (1975), incorporated by reference herein, to a specific activity of 30 Ci/g and 20% specific binding of radioactivity to an excess of FSH receptor as determined according to Catt, et al., *Methods in Receptor Research* (Belcher, ed. 1976) 175–250, incorporated by reference herein. Triplicate aliquots of 100 μl each of the cell suspension (containing approximately 200,000 cells each) were incubated in the presence of 3.13, 6.25, 12.5, 25, 50, or 100 ng of radiolabelled rhFSH in a total volume of 250 μl. Non-specific binding was determined in the presence of 1.5 IU rhFSH. After overnight incubation at room temperature, radioactivity was measured in a gamma spectrometer.

Figure 7:
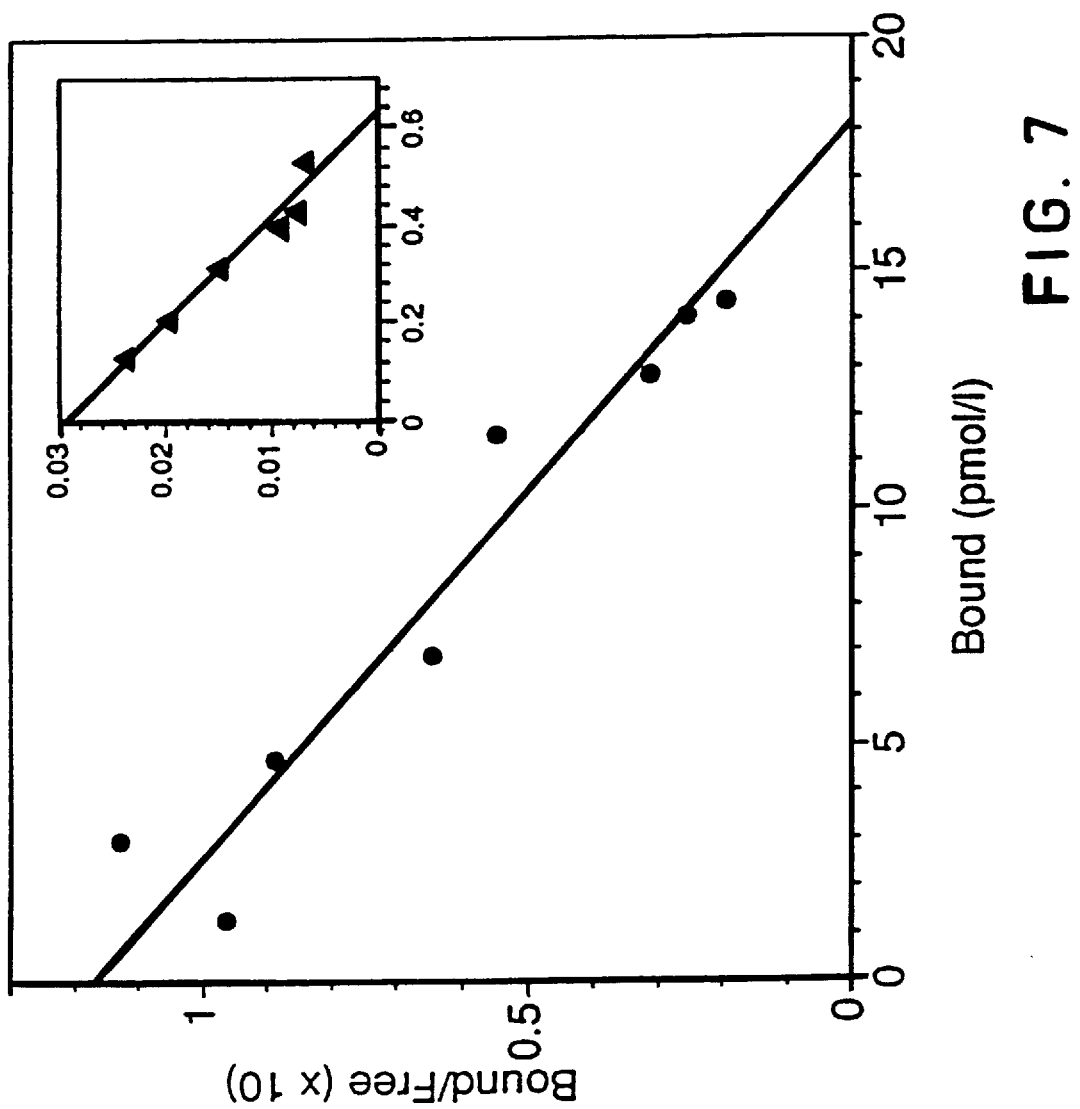
FIG. 7 is a graph showing scatchard analysis of FSH binding to MSC-1 cells transfected with wild-type or mutated FSH receptor-encoding DNA.

Scatchard analysis revealed a 28-fold increase in binding of FSH to cells which had been transfected with wild-type FSH receptor-encoding DNA compared to cells transfected with DNA encoding the C640T allele. The equilibrium constant of FSH binding was $K_a=6.7\times10^9$ L/mol for the wild-type receptor and $4.8\times10^9$ L/mol for the mutated receptor. Results are shown in FIG. 7, wherein circles represent wild-type receptors and triangles represent mutant receptors. In each case specific binding was equalized to a constant amount of luciferase activity. As shown in FIG. 7, specific binding was 18.2 pmol/L for the wild type and 0.63 pmol/L for the ovarian dysgenesis allele.

The foregoing results show that a mutation from C to T at position 640 of the FSH receptor coding sequence is responsible for ovarian dysgenesis in human females and that because that mutation abolishes a BsmI site, digestion with BsmI or another restriction endonuclease which recognizes the BsmI site is useful as a diagnostic tool for ovarian dysgenesis. It is apparent from the foregoing that other mutations may also produce the ovarian dysgenesis phenotype. Comparison of the nucleotide sequence of the FSH receptor gene in those cases with the wild-type sequence also provides a basis for diagnosis of the disease.

---

We claim:

1. A method for diagnosing ovarian dysgenesis in a female patient, comprising the steps of:

obtaining a cell sample from a female patient;

isolating nucleic acids from said cell sample;

amplifying a portion of said nucleic acids, said portion encoding a receptor for follicle-stimulating hormone, thereby generating amplified DNA;

exposing said amplified DNA to a restriction endonuclease selected from the group consisting of BsmI and restriction endonucleases having a recognition site which overlaps that of BsmI, under conditions wherein said restriction endonuclease specifically cleaves DNA at its recognition site;

detecting polynucleotide restriction fragments of said amplified DNA; and diagnosing ovarian dysgenesis from said restriction fragments, wherein ovarian dysgenesis is correlated with a C to T mutation in codon 189 of DNA encoding a human receptor for follicle-stimulating hormone, said mutation eliminating a recognition site of said restriction endonuclease, whereby the absence of restriction fragments that are indicative of cleavage at said recognition site by said restriction endonuclease is an indication of ovarian dysgenesis.

2. A method for diagnosing ovarian dysgenesis in a female patient comprising the steps of:

obtaining a cell sample from a female patient;

isolating nucleic acids from said cell sample;

amplifying a portion of said nucleic acids, said portion comprising exon 7 of a follicle-stimulating hormone receptor gene, said portion excluding any BsmI site outside of exon 7, thereby generating amplified DNA;

exposing said amplified DNA to a restriction endonuclease selected from the group consisting of BsmI and restriction endonucleases having a recognition site which overlaps that of BsmI, under conditions wherein said restriction endonuclease specifically cleaves DNA at its recognition site;

detecting said amplified DNA or polynucleotide restriction fragments thereof after said exposing step; and diagnosing ovarian dysgenesis from said detecting step, wherein ovarian dysgenesis is correlated with the detection of said amplified DNA and the absence of polynucleotide restriction fragments thereof.

3. The method according to claim 1 or 2, wherein said restriction endonucleases having a recognition site which overlaps that of BsmI are selected from the group consisting of SacIII and SstIII.

4. A method for diagnosing ovarian dysgenesis in a female patient comprising the steps of:

obtaining a cell sample from a female patient;

isolating nucleic acids from said cell sample;

amplifying a portion of said nucleic acids, said portion comprising exon 7 of a follicle-stimulating hormone receptor gene, said portion excluding any BsmI site outside of exon 7, thereby generating amplified DNA;

exposing said amplified DNA to a restriction endonuclease selected from the group consisting of BsmI and restriction endonucleases having a recognition site which overlaps that of BsmI, under conditions wherein said restriction endonuclease specifically cleaves DNA at its recognition site;

detecting said amplified DNA or polynucleotide restriction fragments thereof after said exposing step; and diagnosing ovarian dysgenesis from said detecting step, wherein ovarian dysgenesis is correlated with the detection of said amplified DNA and the absence of polynucleotide restriction fragments thereof.

5. The method according to claim 4, wherein said one or more differences between the sequence of said amplified DNA and SEQ ID NO: 1 comprises a difference at nucleotide position 640 in SEQ ID NO: 1.

6. The method according to claim 4, wherein said one or more sequence differences between the sequence of said amplified DNA and SEQ ID NO: 1 includes a T at a position in said amplified DNA corresponding to the C at position 640 in SEQ ID NO: 1.

7. A method for determining a follicle-stimulating hormone receptor (fshr) genotype in a human patient, comprising the steps of:

(a) providing a biological sample comprising nucleic acid from said patient, said nucleic acid including said patient's fshr alleles;

(b) analyzing said nucleic acid for the presence of a mutation or mutations in codon 189 of said fshr alleles; and (c) determining an fshr genotype from said analyzing step, wherein the presence of a mutation in codon 189 of a fshr allele is correlated with an ovarian dysgenesis genotype.

8. The method according to claim 7 wherein said biological sample is a cell sample.

9. The method according to claim 7 wherein said patient is a female.

10. The method according to claim 7 wherein said analyzing comprises sequencing a portion of said nucleic acid, said portion comprising codon 189 of said fshr alleles.

11. The method according to claim 7 wherein said nucleic acid is DNA.

12. The method according to claim 11 wherein said analyzing step comprises the steps of:

(a) exposing said nucleic acid to a restriction endonuclease having a recognition site that includes codon 189 of a wild type fshr allele, under conditions wherein said restriction endonuclease specifically cleaves DNA at its recognition site; and (b) detecting the polynucleotide restriction fragments of said exposing step.

13. The method according to claim 12 wherein said restriction endonuclease is selected from the group consisting of BsmI, restriction endonucleases recognizing sites that overlap a BsmI site, restriction endonucleases recognizing the same cleavage sites as BsmI, and isoschizomers of BsmI.

14. The method according to claim 12 wherein said restriction endonuclease is BsmI.

15. A method for screening for an ovarian dysgenesis genotype in a patient, comprising the steps of:

(a) providing a biological sample comprising nucleic acid from said patient, said nucleic acid including said patient's follicle-stimulating hormone receptor (fshr) alleles;

(b) amplifying a portion of said nucleic acid to generate amplified DNA, said portion including codon 189 of said fshr alleles;

(c) exposing said amplified DNA to a restriction endonuclease selected from the group consisting of BsmI restriction endonuclease and restriction endonucleases having a recognition site which overlaps a BsmI recognition site, under conditions wherein said restriction endonuclease specifically cleaves DNA at the recognition site of said restriction endonuclease;

(d) thereafter detecting said amplified DNA or restriction fragments thereof;

(e) comparing the amplified DNA or fragments thereof of step (d) to control nucleic acid of a human subject free of an ovarian dysgenesis genotype, wherein said control nucleic acid has been amplified, exposed, and detected in accordance with steps (b), (c), and (d); and (f) screening for an ovarian dysgenesis genotype from said comparison, wherein an ovarian dysgenesis genotype in said patient is correlated with a different number of detected amplified DNA or restriction fragments thereof from said patient's amplified DNA than from said control amplified DNA.

16. The method according to claim 15 wherein in said screening step a homozygous ovarian dysgenesis genotype is correlated with fewer detected restriction fragments from said patient's amplified DNA than from said control amplified DNA.

17. The method according to claim 15 wherein in said screening step a heterozygous ovarian dysgenesis genotype is correlated with a greater number of detected amplified DNA or restriction fragments thereof from said patient's amplified DNA than from said control amplified DNA.

18. The method according to claim 15 wherein said patient is a human female.

19. The method according to claim 7 wherein said portion comprises exon 7 of said fshr alleles.

* * * * *